(12) United States Patent
Hanby (10) Patent No.: US 10,077,654 B2
(45) Date of Patent: Sep. 18, 2018

(54) PLATFORM DEVICE FOR SAMPLING AND CHEMICAL REACTION SPECTROPHOTOMETRY OF DRILLING FLUID (71) Applicant: Charles D. Fator, Katy, TX (US)

(72) Inventor: John David Hanby (73) Assignee: Charles D. Fator, Katy, TX (US)

( * ) Notice: Subject to any disclaimer, the term of this patent is extended or adjusted under 35 U.S.C. 154(b) by 115 days.

(21) Appl. No.: 14/992,463

(22) Filed: Jan. 11, 2016

(65) Prior Publication Data
US 2016/0201458 A1 Jul. 14, 2016

Related U.S. Application Data (60) Provisional application No. 62/101,433, filed on Jan. 9, 2015.

(51) Int. Cl.
E21B 49/08 (2006.01)
E21B 49/00 (2006.01)
E21B 21/01 (2006.01)
G01N 21/78 (2006.01)
G01N 33/28 (2006.01)

(52) U.S. Cl.
CPC .......... *E21B 49/005* (2013.01); *E21B 21/01* (2013.01); *E21B 49/086* (2013.01); *G01N 21/78* (2013.01); *G01N 33/2823* (2013.01); *G01N 2201/065* (2013.01); *G01N 2201/129* (2013.01)

(58) Field of Classification Search
None
See application file for complete search history.

(56) References Cited

FOREIGN PATENT DOCUMENTS

WO WO 2013109964 A1 * 7/2013 ......... G01N 33/1833

* cited by examiner

*Primary Examiner* — Paul Sang Hwa Hyun
(74) *Attorney, Agent, or Firm* — Conley Rose, P.C.

(57) ABSTRACT

A spectrometric analysis system for use with a drilling and production system including a first inlet configured to receive an aliquot of downhole drilling fluid, a downhole mixing chamber in fluid communication with the first inlet and a reservoir configured to provide an aliquot of solvent, a second inlet configured to receive an aliquot of uphole drilling fluid, an uphole mixing chamber in fluid communication with the second inlet, a catalyst tape configured to be displaced in the downhole and uphole mixing chambers, an optical device configured to produce a chromophoric signal by contacting the catalyst tape with an electromagnetic signal, and a spectrometer for detecting the chromophoric signal produced by the optical device.

20 Claims, 4 Drawing Sheets

PLATFORM DEVICE FOR SAMPLING AND CHEMICAL REACTION SPECTROPHOTOMETRY OF DRILLING FLUID

CROSS-REFERENCE TO RELATED APPLICATIONS

This application claims benefit of U.S. provisional patent application Ser. No. 62/101,433 filed Jan. 9, 2015, and entitled "Platform Device For Sampling And Chemical Reaction Spectrophotometry Of Drilling Fluid," which is hereby incorporated herein by reference in its entirety for all purposes.

STATEMENT REGARDING FEDERALLY SPONSORED RESEARCH OR DEVELOPMENT

Not applicable.

BACKGROUND

The present disclosure relates generally to the analysis of fluids used in the drilling of oil and gas wells and fluids from subterranean formations. More particularly, the disclosure is directed to devices for spectrometric analysis of hydrocarbons. Generally, robust chromophores in the ultraviolet and visible regions of the electromagnetic spectrum may be produced by Friedel-Crafts Reactions, hereinafter FCRs, with a wide variety of the chemical constituents in crude oil and crude oil fractions. These chromophores may serve as spectral markers to form unique spectrograms or spectral fingerprints for the chemical components in a hydrocarbon or petroleum substance. These unique spectrograms may permit determination of the source of the hydrocarbon or petroleum substances. Still further, this fingerprinting of the petroleum substance may be used for information related to the oil and gas exploration and production industry.

Previously, FCRs have been utilized in kits for detection of hydrocarbon contamination in environmental and geological formation samples. However, such kits have not been used as part of oil and gas exploration and drilling operations. For instance, in oil and gas drilling operations it is common for drilling mud to be pumped from a drilling platform through a drill string disposed in a borehole extending into a subterranean formation. Once circulated through the drill string, the drilling fluid or mud is typically recirculated to the drilling platform via an annulus formed between the inner surface of the borehole and the outer surface of the drill string. Often, fluids from the formation leach into the drilling mud from the borehole wall as the drilling mud is recirculated to the surface. FCR spectrometric analysis kits have been utilized to spectrometrically analyze drilling and formation fluids that are circulated during oil and gas drilling operations.

Accordingly, there remains a need in the art for systems and methods directed towards spectrometrically analyzing drilling and formation fluids as part of oil and gas exploration and drilling operations. Such systems and methods would be well received if they spectrophotometrically identify the presence of formation fluids leached into the drilling mud of an oil and gas drilling operation as drilling mud is circulated through a borehole extending into the formation. Such systems and methods would be particularly well received if they identify the type and amount of formation fluids entering the borehole through spectrophotometric analysis.

SUMMARY

An embodiment of a spectrometric analysis system for use with a drilling and production system comprises a first inlet configured to receive an aliquot of downhole drilling fluid, a downhole mixing chamber in fluid communication with the first inlet and a reservoir configured to provide an aliquot of solvent, a second inlet configured to receive an aliquot of uphole drilling fluid, an uphole mixing chamber in fluid communication with the second inlet, a catalyst tape configured to be displaced in the downhole and uphole mixing chambers, an optical device configured to produce a chromophoric signal by contacting the catalyst tape with an electromagnetic signal, and a spectrometer for detecting the chromophoric signal produced by the optical device. In some embodiments, the system further comprises a roller system coupled to the catalyst tape and configured to displace the catalyst tape between the downhole mixing chamber and uphole mixing chamber over a period of time substantially equal to a recirculation travel time of drilling fluid through a drill string and a borehole of the drilling and production system. In some embodiments, the catalyst tape comprises a catalyst configured to produce Friedel-Crafts reactions in response to contacting an extract solution disposed in the downhole mixing chamber and uphole mixing chamber. In certain embodiments, the spectrometer is configured to detect a downhole chromophoric signal produced from contact between the catalyst and a downhole drilling fluid disposed in the downhole mixing chamber, and an uphole chromophoric signal produced from contact between the catalyst and an uphole drilling fluid disposed in the uphole mixing chamber. In certain embodiments, the spectrometer is configured to compare the downhole chromophoric signal with the uphole chromophoric signal. In some embodiments, the spectrometer is configured to compare the downhole and uphole chromophoric signals using a multivariate analysis algorithm to determine a difference in hydrocarbon content between the downhole and uphole chromophoric signals.

An embodiment of a drilling and production system comprises a drilling rig, a drill string extending from the drilling rig and into a borehole extending through a subterranean formation, an inlet conduit configured to supply drilling fluid to an upper end of the drill string for circulation into the borehole, a return conduit configured to receive drilling fluid exiting the borehole, and a spectrometric analysis system, comprising a first inlet in fluid communication with the inlet conduit, an second inlet in fluid communication with the return conduit, a catalyst system configured to contact a catalyst with downhole drilling fluid flowing through the inlet conduit and uphole drilling fluid flowing through the return conduit, an optical device configured to produce a chromophoric signal by contacting the catalyst of the catalyst system with an electromagnetic signal, and a spectrometer for detecting the chromophoric signal produced by the optical device. In some embodiments, the catalyst system comprises a catalyst tape displaceable between a downhole mixing chamber in fluid communication with the first inlet and an uphole mixing chamber in fluid communication with the second inlet using a roller system coupled to the catalyst tape. In some embodiments, the roller system is configured to displace the catalyst tape between the downhole mixing chamber and uphole mixing chamber over a period of time substantially equal to a recirculation travel time of drilling fluid through the drill string and the borehole. In certain embodiments, the catalyst is configured to produce Friedel-Crafts reactions in response to contacting an extract solution disposed in the downhole mixing chamber and uphole mixing chamber. In certain embodiments, the spectrometer is configured to detect a downhole chromophoric signal produced from contact between the catalyst and a downhole drilling fluid disposed in the downhole mixing chamber, and an uphole chromophoric signal produced from contact between the catalyst and an uphole drilling fluid disposed in the uphole mixing chamber. In some embodiments, the spectrometer is configured to compare the downhole chromophoric signal with the uphole chromophoric signal. In some embodiments, the spectrometer is configured to compare the downhole and uphole chromophoric signals using a multivariate analysis algorithm to determine a difference in hydrocarbon content between the downhole and uphole chromophoric signals.

An embodiment of a method of spectrometrically analyzing a drilling fluid as part of a drilling and production system comprises sampling a downhole drilling fluid, producing downhole Friedel-Crafts reaction products from the sampled downhole drilling fluid, detecting a downhole chromophoric signal from the downhole Friedel-Crafts reaction products, sampling an uphole fluid, producing uphole Friedel-Crafts reaction products from the sampled uphole drilling fluid, and detecting an uphole chromophoric signal from the uphole Friedel-Crafts reaction products. In some embodiments, the method further comprises comparing the uphole chromophoric signal with the downhole chromophoric signal. In some embodiments, the method further comprises comparing the downhole and uphole chromophoric signals using a multivariate analysis algorithm to determine a difference in hydrocarbon content between the downhole and uphole chromophoric signals. In certain embodiments, the method further comprises displacing a catalyst tape between a downhole mixing chamber containing the sampled downhole drilling fluid and an uphole mixing chamber containing the sampled uphole drilling fluid over a period of time substantially equal to a recirculation travel time of drilling fluid through a drill string and a borehole of the drilling and production system. In certain embodiments, the method further comprises sampling a drilling fluid prior to flowing into a drill string of the drilling and production system, and sampling the same drilling fluid after the drilling fluid exits a borehole of the drilling and production system. In some embodiments, the method further comprises producing a downhole spectrogram from the downhole chromophoric signal and an uphole spectrogram from the uphole chromophoric signal. In some embodiments, the method further comprises contacting the uphole and downhole Friedel-Crafts reaction products with an electromagnetic signal from an integrating sphere.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Generally, the analytical spectral data produced by the disclosure herein is related to U.S. Pat. No. 4,992,379 previously granted to the present inventor, and to U.S. application Ser. No. 14/732,295 filed Jul. 18, 2014, each of which is incorporated fully by reference herein. The disclosure of the '379 patent relates to a device and method for qualitative and quantitative analysis of aromatic compounds in water resultant from a FCR, more specifically a Lewis-acid catalyzed FCR, for application in a Chemical Reaction Spectrometric (CRS) device or kit. Further, the disclosure therein generally relates to a method whereby a sample to be tested is extracted, the FCR is catalyzed, and the reaction product is analyzed based on the color and intensity thereof to determine aromatic or hydrocarbon components. The disclosure of the '295 application relates generally to devices and methods for spectrometric analysis of hydrocarbon contaminants in environmental and geological samples. In particular, the disclosure of the '295 application relates to analytical devices and methods for processing catalyst tape in order to generate a spectrogram indicative of contaminants in soil and ground water.

The present disclosure is based on the generation of robust, transient chromophores generated by sigma and pi electrons that engage in bond formation in FCRs. These chromophores resonate with frequencies in the near ultraviolet (UV) and visible (Vis) portions of the electromagnetic spectrum generated by a tungsten/halogen energy source, such as but not limited to approximately the 380-700 nanometer wavelengths of the electromagnetic spectrum. In the present method and apparatus a fluid sample is extracted with an alkyl halide extractant, such as but not limited to carbon tetrachloride. The extract solution is then caused to undergo FCRs by exposure to a Lewis-acid catalyst such as but not limited to anhydrous Aluminum Chloride. This disclosure describes the apparatus that can accept the sample(s), the extraction solvent, a mechanism for introducing the sample(s) and solvent into an extraction chamber, a mechanism for presenting a precise amount of the catalyst to the extracted sample solution, a tungsten/halogen source, and a spectrophotometer for the detection of the signal generated by the FC-produced chromophores.

An embodiment of the spectrometric analysis system of the present disclosure is generally configured to spectrometrically analyze fluids used in oil and gas exploration, drilling, and production operations. In particular, the spectrometric analysis system is configured to spectrometrically analyze drilling fluids that are circulated into and out of a borehole extending into a subterranean formation as part of an oil and gas drilling operation. Specifically, the spectrometric analysis system is configured to spectrometrically analyze drilling fluids by producing an extract solution from a drilling fluid sample using an extractant, causing the extract solution to undergo FCRs by exposure to a catalyst, and detecting electromagnetic signals generated by the FCRs. The spectrometric analysis system is further configured to identify the type and amount of different types of hydrocarbons present in the recirculated drilling fluid through spectrometric analysis of the drilling fluid.

For instance, in an embodiment the spectrometric analysis system is configured to form an input or baseline measurement by spectrometrically analyzing a sample of input drilling fluid flowing into a borehole extending into a subterranean formation, form an output measurement by spectrometrically analyzing a sample of output drilling fluid flowing out of the borehole, and form a comparison by comparing the output measurement with the input measurement. In this embodiment, the spectrometric analysis system may be further configured such that the measurement of the input drilling fluid and output drilling fluid are synchronized. For instance, upon the measurement of the input drilling fluid, the measurement of the drilling fluid may be timed to account for the depth of the borehole and the flow rate of the drilling fluid such that approximately the same drilling fluid is measured both entering and exiting the borehole.

An embodiment of a spectrometric analysis system generally includes a housing having a first inlet configured to provide the housing with a sample of drilling fluid flowing into a borehole (i.e., flowing downhole) extending into a subterranean formation, and a second inlet configured to provide the housing with a sample of drilling fluid that has been circulated through the borehole, and is now flowing out of the borehole (i.e., flowing uphole). In this embodiment, the spectrometric analysis system is generally configured to spectrometrically analyze the samples of downhole and uphole drilling fluids by mixing each of the samples with an extractant, providing a downhole extract solution and an uphole extract solution, and then contacting each extract solution with a catalyst to produce FCRs that may be measured and compared spectrometrically using a spectrophotometer. In this embodiment, the housing of the spectrometric analysis system may include cassette or drum configured to store catalyst tape and a roller assembly configured to displace the catalyst tape from the cassette, through a portion of the housing, and deposit the tape in a waste chamber.

The catalyst tape may be configured to transfer one or more encapsulated reagents that form a linear series of discrete reaction vessels. In this configuration, the encapsulated reaction vessels comprise a tape or tube that is configured for serial or sequential processing of each of the discrete reaction vessels in individual fashion. In exemplary embodiments, the tape or tube may be configured as a roll, a drum, or a coil without limitation, and configurable to unwind during processing of each discrete reaction vessel.

The housing may also include a solvent reservoir for storing a solvent and a solvent pump for displacing the solvent to a mixing chamber disposed in the housing. In this embodiment, the mixing chamber is configured to mix the solvent displaced through the solvent pump with a drilling fluid sample, forming a solution extract. The mixing chamber may be further configured to contact the extract solution with the catalyst tape, causing FCRs to occur as the extract solution flows into one or more encapsulated reaction vessels of the catalyst tape, forming an encapsulated reaction therein. The housing may further include an optical device configured to contact the encapsulated reaction with an electromagnetic signal, and to measure the absorption of the electromagnetic signal in the encapsulated reaction across a segment of the electromagnetic spectrum, including the near UV and Vis portions of the electromagnetic spectrum.

In an embodiment, the optical device may generally include a light source and a light receiver that are disposed within an analysis compartment. The light source may be an optical probe or emitter such as a laser device or a fiber optic device. Further, the light source may include a filter or other apparatus configured to alter the light properties to irradiate the encapsulated reaction. The light receiver is generally configured to convert the light emitted from the irradiated encapsulated reaction into a graphical format or a data format. Exemplary light receivers may be cameras or photon collecting, counting, or capturing devices and arrays. In some configurations, the light receiver may include a filter, a grating, or another apparatus configured to alter the light properties emitted from the encapsulated reaction. In an embodiment, the optical device may comprise an integrating sphere having a hollow spherical cavity with the light source disposed therein, and apertures for the passing of electromagnetic signals to the encapsulated reaction and the light receiver.

Figure 1:
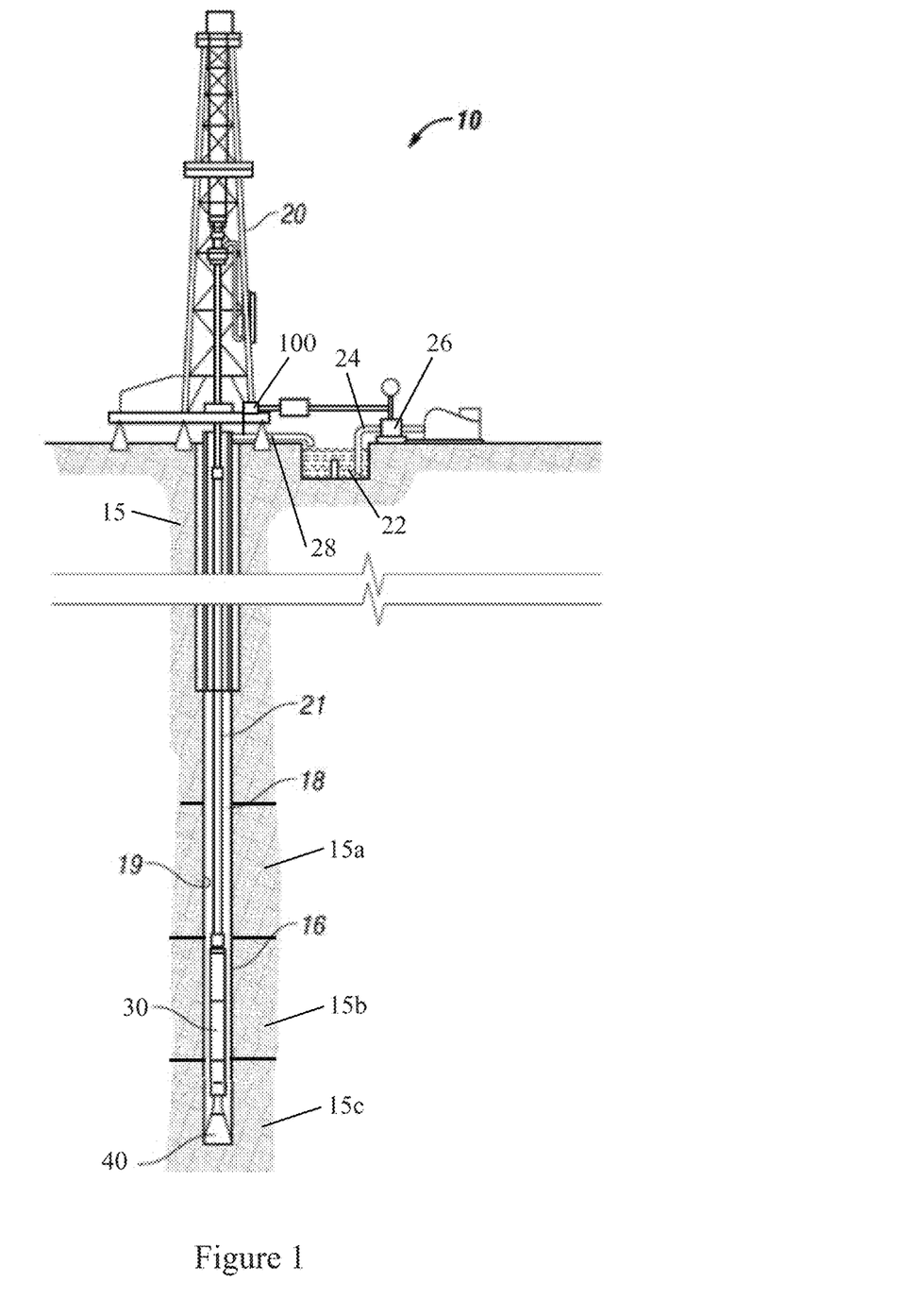
FIG. 1 illustrates a schematic view of an oil and gas drilling system in accordance with principles disclosed herein.

Referring now to FIG. 1, a system 10 for drilling for drilling a borehole 16 in a subterranean formation 15 is shown. In this embodiment, system 10 includes a drilling rig 20 disposed at the surface, a drill string 21 extending downhole from rig 20, a bottomhole assembly (BHA) 30 coupled to the lower end of drillstring 21, and a drill bit 40 attached to the lower end of BHA 30. A power section in BHA 30 converts the fluid pressure of the drilling fluid pumped downward through drillstring 21 into rotational torque for driving the rotation of drill bit 40. A drive shaft assembly transfers the torque to bit 40. With force or weight applied to the drill bit 40, also referred to as weight-on-bit ("WOB"), the rotating drill bit 40 engages the formation 15 and proceeds to form borehole 16 along a predetermined path toward and through one or more pay or target zones, shown as zones 15a, 15b, and 15c in FIG. 1.

Drilling fluid is stored in a reservoir 22 proximal to platform 20 at the surface of formation 15. Drilling fluid from reservoir 22 is pumped into drillstring 21 via an inlet conduit 24 and mud pump 26 disposed on the platform 20. The drilling fluid or mud pumped down the drill string 21 and through a downhole motor in the BHA 30, passes out of the face of drill bit 40 and back up the annulus 18 formed between drill string 21 and the wall 19 of borehole 16. The drilling fluid cools the bit 40, flushes the cuttings away from the face of bit 40, and returns the drilling fluid to the reservoir 22 via a return conduit 28. An embodiment of a spectrometric analysis system 100 is also disposed on rig 20, and is in fluid communication with both the inlet conduit 24 and the return conduit 28. The spectrometric analysis system 100 is generally configured to spectrometrically or spectrophotometrically analyze a sample of drilling fluid entering the drillstring 21 via inlet conduit 24 and a sample of drilling fluid exiting borehole 16 via return conduit 28

To drill a straight section of borehole 16, drillstring 21 is rotated from rig 20 with a rotary table or top drive to rotate BHA 30 and drill bit 40 coupled thereto. Drillstring 21 and BHA 30 rotate about the longitudinal axis of drillstring 21, and thus, drill bit 40 is also forced to rotate about the longitudinal axis of drillstring 21. During an oil and gas drilling and production operation, the borehole 16 may be drilled into a target zone, such as target zone 15a, and the formation fluids produced from zone 15a into the borehole 16 may be measured for hydrocarbon content. For instance, a sample of drilling fluid may be communicated to system 100 via inlet conduit 22 and spectrometrically analyzed, producing an inlet spectrogram. Following a predetermined length of time dependent upon the depth of borehole 16 and the flow rate of the drilling fluid, a second sample of drilling fluid may be communicated to system 100 via outlet conduit 28 and spectrometrically analyzed, producing an outlet spectrogram. Following this, the inlet and outlet spectrograms are compared using a multivariate analysis algorithm to determine if, and how many, hydrocarbons have flowed into the returning drilling fluid from the formation 15.

Depending upon the results of the spectrometric analysis performed by system 100, the drillstring 21 may be removed from borehole 16 to allow the insertion of a production string to produce formation fluid from target zone 15a to the surface of formation 15. Following sufficient production of hydrocarbons from target zone 15a, the production string may be uninstalled, and drillstring 21 may be reinstalled into the borehole, and the borehole may be drilled until reaching target zone 15b, where the steps described above may be repeated.

Figure 2:
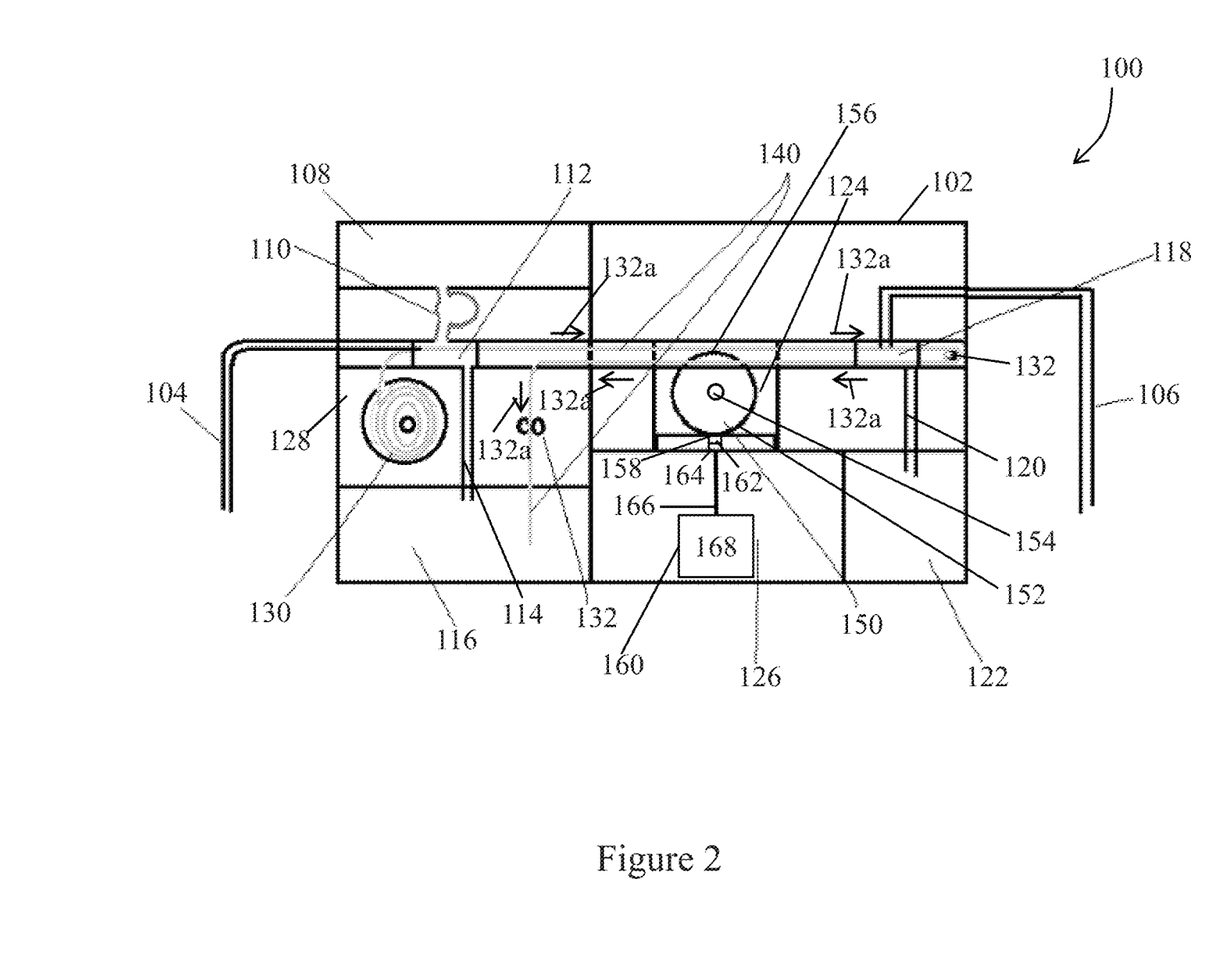
FIG. 2 illustrates a schematic view of an embodiment of a spectrometric analysis system in accordance with principles disclosed herein.

Referring to FIG. 2, the spectrometric analysis system 100 generally includes a housing having a first or downhole drilling fluid inlet 104 in fluid communication with inlet conduit 22 and a second inlet or uphole drilling fluid inlet 106 in fluid communication with return conduit 28. The downhole inlet 104 is configured to insert or inject a sample of drilling fluid entering drillstring 21 to the system 100, and the uphole inlet 106 is configured to insert or inject a sample of drilling fluid exiting borehole 16 to the system 100. In an embodiment, inlets 104 and 106 are each comprise approximately ⅛" stainless steel tubing and are configured to each inject an aliquot of approximately 0.250 milliliters of sample drilling fluid. In this embodiment, the housing 102 of spectrometric analysis system 100 also includes a solvent reservoir chamber 108, a solvent pump 110, a first or downhole mixing chamber 112, a first or downhole waste conduit 114, a first or downhole waste chamber 116, a second or uphole mixing chamber 118, a second or uphole waste conduit 120, a second or uphole waste chamber 122, an optical device chamber 124, a spectrometer chamber 126, and a catalyst tape storage chamber 128. The housing 102 further includes a catalyst tape storage cassette or drum 130 disposed in catalyst tape storage chamber 128, wherein the storage cassette 130 stores at least a portion of catalyst tape 140, a roller assembly or system 132, an optical device 150 disposed in optical device chamber 124, and a spectrometer 160 disposed in spectrometer storage chamber 126. In an embodiment, cassette 130 stores approximately 200 centimeters of catalyst tape 140. In an embodiment, catalyst tape 140 and roller assembly 132 comprise a catalyst system.

Figure 3:
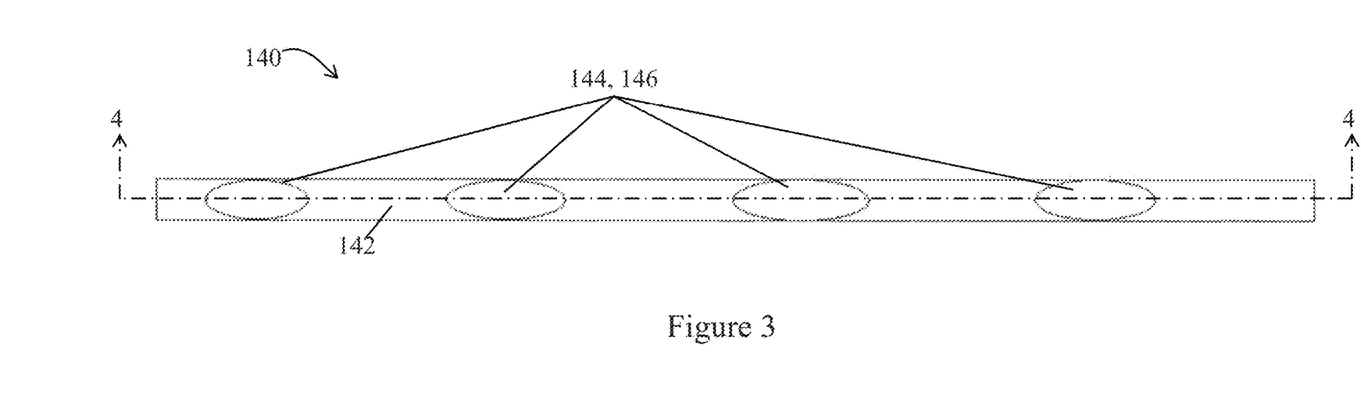
FIG. 3 illustrates a top view of an embodiment of catalyst tape in accordance with principles disclosed herein.
Figure 4:
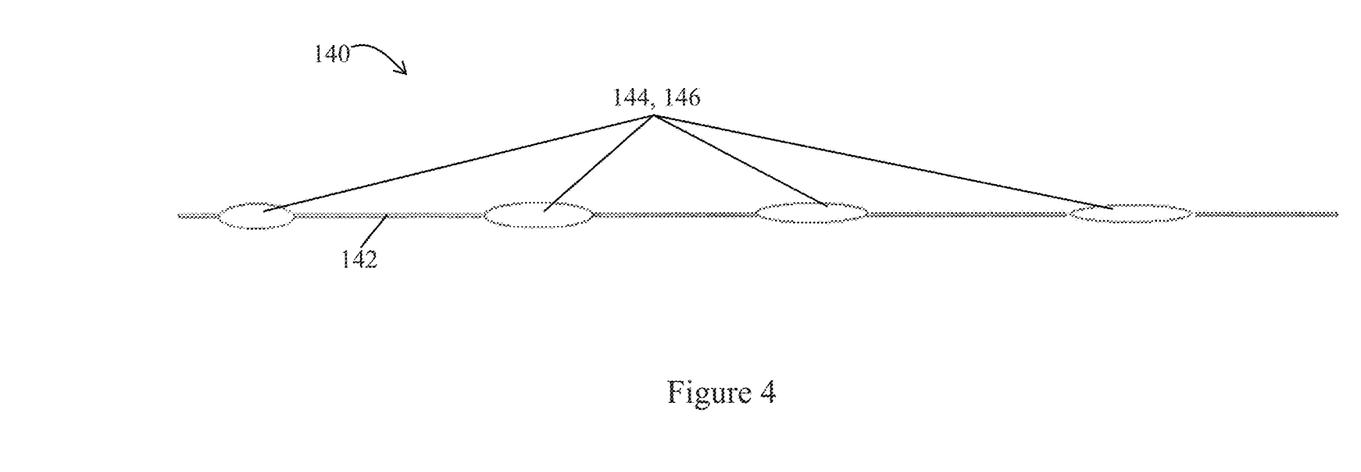
FIG. 4 illustrates a cross-sectional side view along line 4-4 of the catalyst tape of FIG. 3.

Referring to FIGS. 3 and 4, the catalyst tape 140 is configured to isolate reagents 144 and includes a material 142 configurable for the induced, selective, selectively permeable, or semipermeable passage of fluids therethrough. In exemplary configurations, the material 142 is a polymeric material or film. The material 142 includes a non-reactive polymer, and for example, a hydrophobic polymer such that water is at least temporarily excluded from contacting the reagents 144. Exemplary polymers may include polyethylene, polypropylene, other olefinic polymers, or silicon polymers, without limitation.

As discussed hereinabove, the catalyst tape 140 includes reagents 144 captured by and isolated within the material 142. Generally, the reagents 144 are encapsulated within the generally tubular material 142. The reagents 144 include any reactive material for exposure to an analyte or sample. In some configurations, the reagents 144 may exist as solids or liquids. Generally, the reagents 144 include at least one catalyst, for example, a Lewis-acid catalyst. In some configurations, the reagents 144 are a FCR catalyst. Exemplary catalysts include anhydrous acid catalysts and, more specifically, an anhydrous aluminum chloride ($AlCl_3$). The reagents 144 contain predetermined quantities such as concentrations, masses, or volumes of the catalysts. In certain instances, the reagents 144 include stoichiometric concentrations that are predetermined to sufficiently react with a predetermined volume of an analyte. The reagents 144 are selected for the FCR in order to form chromophores with selected analytes.

The reagents 144 are individually sealed via any device configured to thermally or pressurably contact and seal, vulcanize, or bond together the inner surface of the tubular material 142 of catalyst tape 140 between each reagent 144. Thusly configured, the catalyst tape 140 provides single or multiple regularly spaced, discrete reaction vessels 146 for the reagents 144 in the material 142. The catalyst tape 140 provides single or multiple discrete reaction vessels 146 for spectrometric analysis. In an embodiment, the reaction vessels 146 are approximately one centimeter in length and filled with a reagent 142 having a mass of approximately 0.25 grams.

Referring again to FIG. 2, the solvent reservoir chamber 108 includes a partially or totally sealable vessel for retaining a predetermined volume, mass, or concentration of a reaction solvent. In an embodiment, the solvent reservoir 108 is configured to hold approximately one liter of solvent. Generally, the solvent reservoir 108 may comprise any material that is resistant to acid, solvent, hydrocarbon, or other reactive chemical groups, such as alkanes or halides thereof. In an embodiment, the solvent reservoir 108 may be constructed out of poly-vinyl chloride (PVC), polyethylene (PE), polypropylene (PP) or a comparable material. In an embodiment, the solvent disposed in solvent reservoir 108 is a solvent configured for dissolving hydrocarbons, such as but not limited to the solvent carbon tetrachloride ($CCl_4$). The solvent reservoir chamber 108 is coupled to solvent pump 110, which is configured to place reservoir 108 in fluid communication with downhole mixing chamber 112, and to displace or inject an aliquot of solvent from solvent reservoir 108 into downhole mixing chamber 112. In an embodiment, the solvent pump 110 is configured to inject an aliquot of approximately one milliliter of solvent into mixing chamber 112 from solvent reservoir 108.

The roller assembly 132 is generally configured to displace or advance at a controlled or predetermined rate the catalyst tape 140 from the storage cassette 130, through downhole mixing chamber 112, optical device chamber 124, uphole mixing chamber 118, back through optical device chamber 124, and finally into downhole waste chamber 116, as shown by arrows 132a. For instance, the roller assembly 132 is configured to advance the catalyst tape 140 at a rate to synchronize the measurement of downhole and uphole drilling fluid aliquot analytes injected into mixing chambers 112 and 118, respectively, as will be explained in further detail herein. In an embodiment, roller assembly 132 includes a plurality of spring loaded rollers coupled to an electric motor (not shown) for rotating the rollers, which physically engage and pull or displace the catalyst tape 140.

The downhole and uphole mixing chambers 112 and 118, respectively, are generally configured to produce FCRs and FCR products from the analytes injected from inlets 104 and 108, where the FCR products may then be analyzed using the optical device 150 and spectrometer 160. Specifically, downhole mixing chamber 112 receives a small aliquot of solvent from solvent reservoir chamber 108 via solvent pump 110, a small aliquot of analyte from inlet 104, and a small section of catalyst tape 140, which is displaced or pulled by roller assembly 132. Mixing of the solvent supplied by reservoir 108 and analyte from inlet 104 is accomplished via the flow of solvent produced by solvent pump 110 and the flow of analyte entering inlet 104 from inlet conduit 24 (shown in FIG. 1). Contact and mixing between the solvent and analyte produces a downhole extract solution configured to cause FCRs after contacting the reagent 144 stored within reaction vessel 146 of catalyst tape 140 at a precisely controlled temperature and duration determined by the diffusion of the extract solution through the material 142 and into the reaction vessel 146.

Following diffusion of the extract solution into the reaction vessel 146, FCRs are produced by contact between the reagent 144 and aromatic compounds included in the downhole extract solution (assuming hydrocarbons were present in the analyte supplied to the mixing chamber 112), producing downhole FCR products. The FCR products include chromophores that are configured to be analyzable spectrophotometrically. For instance, the FCR products may be analyzed spectrophotometrically, via downhole chromophoric signals emitted by chromophores that resonate in the near UV and Vis portions of the electromagnetic spectrum, for the presence and type of aromatic compounds present within the FCR products. Leftover waste produced by the mixing of solvent from pump 110 and the analyte from inlet 104 is injected into the downhole waste chamber 116 from mixing chamber 112 via downhole waste conduit 114.

As with the solvent reservoir chamber 108, the mixing chamber 112 may comprise any material that is resistant to acid, solvent, hydrocarbon, or other reactive chemical groups, such as alkanes or halides thereof; and in an embodiment, may be constructed out of poly-vinyl chloride (PVC) or a comparable material. In an embodiment, downhole mixing chamber 112 receives a section of catalyst tape 140 approximately one centimeter in length that includes a single reaction vessel 146 and reagent 144. In an embodiment, mixing chamber 112 is maintained at approximately 60° Celsius thermoelectrically (via a thermoelectric heater (not shown), for instance) to allow for proper diffusion of the extract solution into the reaction vessel 146. Similarly, the uphole mixing chamber 118 receives a small aliquot of analyte from uphole inlet 106 and a small section of catalyst tape 140 via roller assembly 132. The roller assembly 132 is configured to provide the same section of catalyst tape 140 provided to downhole mixing chamber 112, and thus, a portion of the aliquot of solvent supplied by solvent pump 110 is still contacting the section of catalyst tape 140. This leftover portion of the aliquot of solvent supplied by pump 110 contacts the analyte supplied by uphole inlet 106 to produce an uphole extract solution. The uphole extract solution is configured to cause FCRs after contacting the reagent 144 stored within same reaction vessel 146 of catalyst tape 140 provided to the downhole mixing chamber 112, at a precisely controlled temperature and duration determined by the diffusion of the extract solution into the reaction vessel 146 through the material 142.

Following diffusion of the uphole extract solution into the reaction vessel 146, FCRs are produced by contact between the reagent 144 and aromatic compounds included in the uphole extract solution (assuming hydrocarbons were present in the analyte supplied to the mixing chamber 118), producing uphole FCR products. As with the downhole FCR products, the uphole FCR products include chromophores that are configured to be analyzable spectrophotometrically via uphole chromophoric signals emitted from the chromophores of the uphole FCR products. Leftover waste disposed in uphole mixing chamber 118 is injected into the uphole waste chamber 122 from mixing chamber 118 via uphole waste conduit 120.

Once downhole FCR products have been created through contact between the downhole extract solution and a section of catalyst tape 140 including a reaction vessel 146 and reagent 144, the particular section of catalyst tape 140 is displaced or pulled by roller assembly 132 into optical device chamber 124 proximal optical device 150. Optical device 150 is generally configured to provide an electromagnetic signal to the spectrometer 160 for spectrophotometric analysis. Specifically, optical device 150 is configured to produce a chromophoric signal from the FCR products and transmit the chromophoric signal to the spectrometer 160. In particular, the optical device 150 is configured to generate an electromagnetic signal, contact the FCR products with the electromagnetic signal to create a chromophoric signal, and transmit the chromophoric signal to the spectrometer 160 for spectrophotometric analysis.

The optical device 150 includes a generally spherical housing 152 configured to diffuse or scatter electromagnetic signals emitted within housing 152 evenly over all angles, and in this way, the flux of an electromagnetic or light source disposed in the housing 152 may be measured by the spectrometer 160 without inaccuracy caused by the directional characteristics of the light source. The optical device further includes a light source 154 disposed within the interior of spherical housing 152, a first or upper aperture 156 disposed proximal to the catalyst tape 140, and a second or lower aperture 158 disposed proximal the spectrometer 160. Light source 154 may be a separate or integral component of housing 152. In some embodiments, light source 154 comprises a halogen or tungsten halogen light source having a broad emission spectrum. Light source 154 may further include other known emissive configurations for projecting excitation light and, in some instances, predetermined wavelengths of light, onto catalyst tape 140. Upper aperture 156 is configured to allow light emitted from light source 154 to be transmitted to and contact the reaction vessel 146 (housing the FCR products) of catalyst tape 140 disposed proximal upper aperture 156, allowing the emitted light to interact with the chromophores of the FCR products to produce a chromophoric signal that is reflected back into the interior of the spherical housing 152, diffused via reflection off of the spherical inner surface of housing 152, and finally transmitted to the lower aperture 158.

Spectrometer 160 is generally configured to receive and detect the chromophoric signal transmitted to lower aperture 158 of optical device 150. In an embodiment, spectrometer 160 is configured to detect a chromophoric electromagnetic signal having a wavelength of approximately between 380-780 nanometers. The spectrometer 160 is also configured to digitize the detected chromophoric signal and analyze the digital signal using a computer or other microprocessor-based device. The spectrometer 160 is further configured to compare the downhole chromophoric signals emitted by the downhole FCR products with the uphole chromophoric signals emitted by the uphole FCR products to determine the change, if any, of the amount and type of hydrocarbons disposed in the drilling fluid as it flows through the length of the borehole. For instance, the spectrometer 160 is configured to compare the downhole and uphole chromophoric signals using a multivariate analysis algorithm.

Spectrometer 160 generally includes a filter 162, a receptor 164, a cable 166, and an analysis device 168. The filter 162 is disposed adjacent to and in the light path of light refracted, transmitted or emitted during chromophore absorbance. The filter 162 includes an optical filter, such as but not limited to a polarizer, a diffraction grating, a chromatic or dichroic lens, or any other optical filter configurable to alter light refracted or transmitted through the sample. In certain instances, the filter 162 may be an electronic device for optical analysis coupled to the receptor 164 via a fiber-optic cable or integral to the receptor 164.

The receptor 164 includes an optical array for collecting photons that pass through the filter 162. Exemplary receptor 164 configurations include cameras, charge coupled devices (CCDs), spectrometers, or mini-spectrometers. The receptor 164 generates a digital output that is conveyed to a analysis device 462 such as a computer via the cable 166. The analysis device 168 is configured to receive, store, and analyze the digitized chromophoric signals transmitted from the receptor 164. The analysis device 168 is also configured to compare the downhole chromophoric signals with the uphole chromophoric signals to determine the change, if any, of the amount and type of hydrocarbons disposed in the drilling fluid as it flows through the length of the borehole. Without limitation by theory, the analysis device 168 includes a processor configured to access instructions stored on a memory, such that when executed, the manipulation, analysis, display, and reproduction of data indicative of the photons impingent on the receptor 164 is possible. In an embodiment, the analysis device 168 may comprise a hard drive or portable processing/storage medium. In some embodiments, the light source 154, receptor 164, and analysis device 168 are components of the same device.

Figure 5:
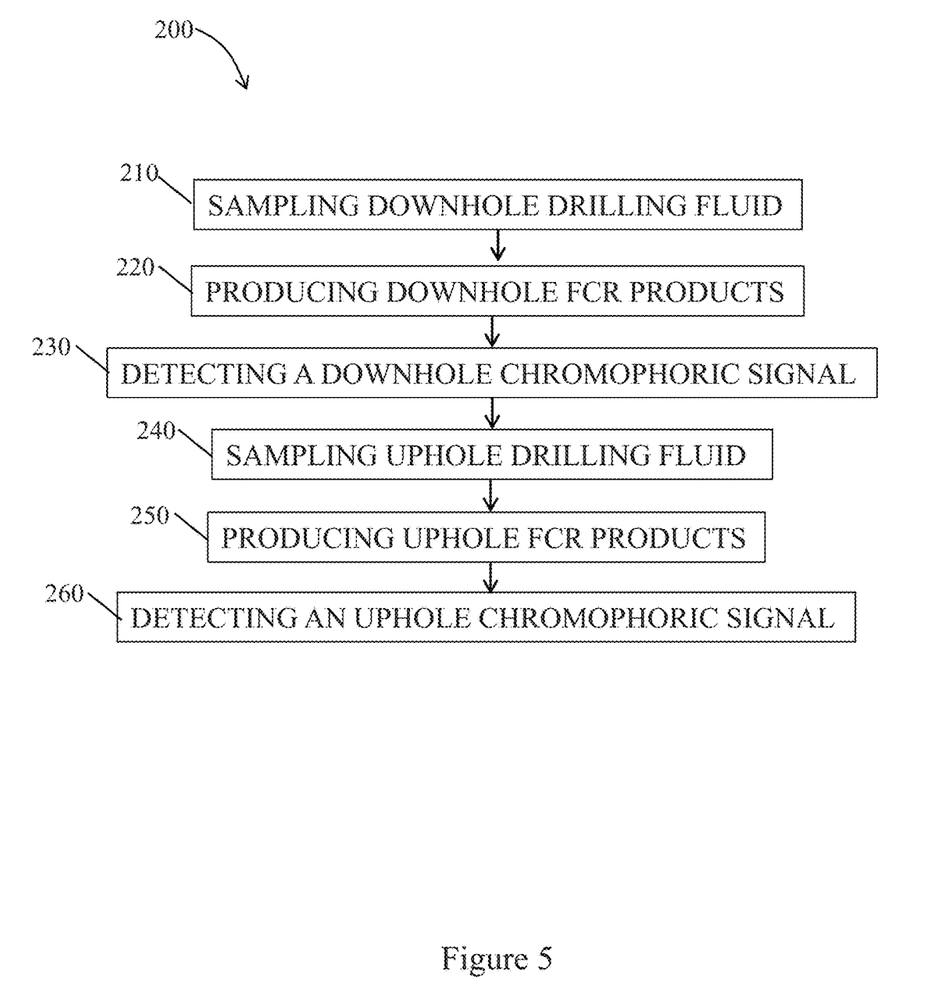
FIG. 5 illustrates a method of analyzing hydrocarbons in accordance with principles disclosed herein.

Referring to FIG. 5, there is illustrated a method 200 for conducting an analysis according to the system described in FIGS. 1-4. At block 210 of method 200, downhole drilling fluid is sampled. In some embodiments, block 210 includes flowing a sample of drilling fluid from inlet conduit 24 (FIG. 1) into inlet 104 (FIG. 2) of spectrometric analysis system 100. In certain embodiments, block 210 further includes producing a downhole extract solution from the sampled downhole drilling fluid. In some embodiments, this may comprise injecting a small aliquot of the downhole drilling fluid analyte in inlet 104 into downhole mixing chamber 112, injecting a small aliquot of solvent from solvent reservoir chamber 108 into mixing chamber 112 via solvent pump 110, and mixing the solvent and analyte in the mixing chamber 112.

At block 220 of method 200, downhole FCR products are produced from the sampled downhole drilling fluid. In some embodiments, block 220 includes contacting the produced downhole extract solution with a section of the catalyst tape 140 having a reaction vessel 146 housing a reagent 144 for a precisely controlled duration and at a controlled temperature determined by the diffusion of the extract solution through the material 142 and into the vessel 146, thereby allowing the downhole extract solution to contact and react with the reagent 144. At block 230 of method 200, a downhole chromophoric signal is detected from the downhole FCR products. In certain embodiments, block 230 includes disposing the downhole FCR products housed in reaction vessel 146 proximal upper aperture 156 of optical device 150, contacting the FCR products disposed in vessel 146 with an electromagnetic signal emitted from the light source 154 disposed in optical device 150 to produce a downhole chromophoric signal, diffusing the downhole chromophoric signal across an inner surface of the spherical housing 152 of the optical device 150, and receiving the diffused downhole chromophoric signal using the spectrometer 160. In some embodiments, block 230 also includes digitizing the chromophoric signal using the receptor 164, and storing and analyzing the digitized downhole chromophoric signal using the analysis device 168. In some embodiments, block 230 also includes producing a downhole spectrogram of the chromophoric signal using the spectrometer 160.

At block 240 of method 200, uphole drilling fluid is sampled. In some embodiments, block 240 includes flowing a sample of drilling fluid from return conduit 24 into inlet 108 of spectrometric analysis system 100. In some embodiments, block 240 also includes timing the sampling of the uphole drilling fluid such that the drilling fluid sampled from return conduit 24 is substantially similar to the drilling fluid sampled from inlet conduit 24 in step 210 of method 200. For instance, a recirculation travel time or duration elapses as the drilling fluid is pumped through inlet conduit 24 into drillstring 21, circulated from the uppermost portion of drillstring 21 at rig 20 to the drill bit 40 proximal the bottom of borehole 16, and recirculated upwards through the annulus 18 of borehole 16 and into return conduit 28. Thus, the time between steps 210 and 250 should be consistent with the recirculation travel time of the drilling fluid to ensure that the same or at least substantially similar drilling fluid is being sampled at steps 210 and 250. It should be noted that the travel time of the drilling fluid is dependent upon the depth of the borehole 15 and the flow rate of the drilling fluid in system 10.

In certain embodiments, block 240 includes producing an uphole extract solution from the sampled uphole drilling fluid. In certain embodiments, this comprises injecting a small aliquot of the uphole drilling fluid analyte in inlet 108 into uphole mixing chamber 118 and disposing the same section of the catalyst tap 140 used at block 220 of method 200 into mixing chamber 118, thereby providing an aliquot of solvent to chamber 118, and mixing the solvent and analyte in the mixing chamber 112. Given that the same section of catalyst tape 140 is used in both blocks 220 and 240, the advancement of the catalyst tape 140 via roller assembly 132 should be at a rate that allows the particular reaction vessel 146 of the section of catalyst tape 140 to traverse between downhole mixing chamber 112 and uphole mixing chamber 118 in a time or duration consistent with the travel time of the drilling fluid, as discussed above. In other words, the temporal duration that occurs during the advancement of catalyst tape 140 between blocks 220 and 240 is substantially equal to the recirculation travel time discussed above.

At block 250 of method 200, uphole FCR products are produced from the sampled uphole drilling fluid. In some embodiments, block 250 includes contacting the produced uphole extract solution with a section of the catalyst tape 140 having a reaction vessel 146 housing a reagent 144 for a precisely controlled duration and at a controlled temperature determined by the diffusion of the extract solution through the material 142 and into the vessel 146, thereby allowing the uphole extract solution to contact and react with the reagent 144. At block 260 of method 200, an uphole chromophoric signal is detected from the uphole FCR products. In certain embodiments, block 260 includes disposing the uphole FCR products housed in reaction vessel 146 proximal upper aperture 156 of optical detector 150, contacting the FCR products disposed in vessel 146 with an electromagnetic signal emitted from the light source 154 disposed in optical device 150 to produce an uphole chromophoric signal, diffusing the uphole chromophoric signal across an inner surface of the spherical housing 152 of the optical device 150, and receiving the diffused uphole chromophoric signal using the spectrometer 160. In certain embodiments, block 260 also includes digitizing the chromophoric signal using the receptor 164, and storing and analyzing the digitized uphole chromophoric signal using the analysis device 168. In some embodiments, block 260 further includes producing an uphole spectrogram of the chromophoric signal using the spectrometer 160.

In some embodiments, method 200 further includes comparing the downhole and uphole chromophoric signals. In some embodiments, comparing the downhole and uphole chromophoric signal includes comparing the chromophoric signals using a multivariate analysis algorithm. In some embodiments, the multivariate analysis algorithm may determine the quantity of hydrocarbons added to the drilling fluid as it is circulated through the borehole 16 during its recirculation travel time by detecting an increase in aromatic compounds between the downhole and uphole chromophoric signals. The multivariate analysis algorithm may also determine the type(s) of hydrocarbons added (i.e., a difference in hydrocarbon content between the downhole and uphole chromophoric signals) to the drilling fluid during its travel time due to the types and amounts of aromatic compounds added to the drilling fluid during its travel time. For instance, different types of crude oils have specific or particular spectrograms when analyzed spectrophotometrically due to having specific quantities and types of aromatic compounds. Thus the multivariate analysis algorithm may determine the presence of particular type(s) of crude oil(s) present in the drilling fluid by comparing its analysis of the downhole and uphole chromophoric compounds (including the creation of uphole and downhole spectrograms) with spectrograms of a set of crude oils.

Many modifications and variations, particularly in regard to automated or remote actuation, as specifically mentioned in the embodied device and method may be made without departing substantially from the concept of the present disclosure. Accordingly, it should be clearly understood that the form of the disclosure described herein is exemplary only, and is not intended as a limitation on the scope thereof.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented. Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A spectrometric analysis system for use with a drilling and production system, comprising:
   a first inlet configured to receive an aliquot of downhole drilling fluid;
   a downhole mixing chamber in fluid communication with the first inlet and a reservoir configured to provide an aliquot of solvent;
   a second inlet configured to receive an aliquot of uphole drilling fluid;
   an uphole mixing chamber in fluid communication with the second inlet and configured to receive the aliquot of uphole drilling fluid from the second inlet;
   a catalyst tape configured to be displaced in the downhole and uphole mixing chambers;
   an optical device configured to produce a chromophoric signal by contacting the catalyst tape with an electromagnetic signal; and
   a spectrometer for detecting the chromophoric signal produced by the optical device.

2. The system of claim 1, further comprising a roller system coupled to the catalyst tape and configured to displace the catalyst tape between the downhole mixing chamber and uphole mixing chamber over a period of time substantially equal to a recirculation travel time of drilling fluid through a drill string and a borehole of the drilling and production system.

3. The system of claim 1, wherein the catalyst tape comprises a catalyst configured to produce Friedel-Crafts reactions in response to contacting an extract solution disposed in the downhole mixing chamber and uphole mixing chamber.

4. The system of claim 1, wherein the spectrometer is configured to detect a downhole chromophoric signal from Friedel-Crafts reaction products produced from contact between the catalyst and a downhole drilling fluid disposed in the downhole mixing chamber, and an uphole chromophoric signal from Friedel-Crafts reaction products produced from contact between the catalyst and an uphole drilling fluid disposed in the uphole mixing chamber.

5. The system of claim 4, wherein the spectrometer is configured to compare the downhole chromophoric signal with the uphole chromophoric signal.

6. The system of claim 5, wherein the spectrometer is configured to compare the downhole and uphole chromophoric signals using a multivariate analysis algorithm to determine a difference in hydrocarbon content between the downhole and uphole chromophoric signals.

7. A drilling and production system, comprising:
   a drilling rig;
   a drill string extending from the drilling rig and into a borehole extending through a subterranean formation;
   an inlet conduit configured to supply drilling fluid to an upper end of the drill string for circulation into the borehole;
   a return conduit configured to receive drilling fluid exiting the borehole; and
   a spectrometric analysis system, comprising:
      a first inlet in fluid communication with the inlet conduit;
      an second inlet in fluid communication with the return conduit;
      a catalyst system configured to contact a catalyst with downhole drilling fluid flowing through the inlet conduit and uphole drilling fluid flowing through the return conduit;
      an optical device configured to produce a chromophoric signal by contacting the catalyst of the catalyst system with an electromagnetic signal; and a spectrometer for detecting the chromophoric signal produced by the optical device.

8. The system of claim 7, wherein the catalyst system comprises a catalyst tape displaceable between a downhole mixing chamber in fluid communication with the first inlet and an uphole mixing chamber in fluid communication with the second inlet using a roller system coupled to the catalyst tape.

9. The system of claim 8, wherein the roller system is configured to displace the catalyst tape between the downhole mixing chamber and uphole mixing chamber over a period of time substantially equal to a recirculation travel time of drilling fluid through the drill string and the borehole.

10. The system of claim 8, wherein the catalyst is configured to produce Friedel-Crafts reactions in response to contacting an extract solution disposed in the downhole mixing chamber and uphole mixing chamber.

11. The system of claim 8, wherein the spectrometer is configured to detect a downhole chromophoric signal from Friedel-Crafts reaction products produced from contact between the catalyst and a downhole drilling fluid disposed in the downhole mixing chamber, and an uphole chromophoric signal from Friedel-Crafts reaction products produced from contact between the catalyst and an uphole drilling fluid disposed in the uphole mixing chamber.

12. The system of claim 11, wherein the spectrometer is configured to compare the downhole chromophoric signal with the uphole chromophoric signal.

13. The system of claim 12, wherein the spectrometer is configured to compare the downhole and uphole chromophoric signals using a multivariate analysis algorithm to determine a difference in hydrocarbon content indicated by the downhole and uphole chromophoric signals.

14. A method of spectrometrically analyzing a drilling fluid as part of a drilling and production system, comprising:
    sampling a downhole drilling fluid;
    producing downhole Friedel-Crafts reaction products from the sampled downhole drilling fluid;
    detecting a downhole chromophoric signal from the downhole Friedel-Crafts reaction products;
    sampling an uphole fluid;
    producing uphole Friedel-Crafts reaction products from the sampled uphole drilling fluid; and
    detecting an uphole chromophoric signal from the uphole Friedel-Crafts reaction products.

15. The method of claim 14, further comprising comparing the uphole chromophoric signal with the downhole chromophoric signal.

16. The method of claim 15, further comprising comparing the downhole and uphole chromophoric signals using a multivariate analysis algorithm to determine a difference in hydrocarbon content indicated by the downhole and uphole chromophoric signals.

17. The method of claim 14, further comprising displacing a catalyst tape between a downhole mixing chamber containing the sampled downhole drilling fluid and an uphole mixing chamber containing the sampled uphole drilling fluid over a period of time substantially equal to a recirculation travel time of drilling fluid through a drill string and a borehole of the drilling and production system.

18. The method of claim 14, further comprising:
    sampling a drilling fluid prior to flowing the drilling fluid into a drill string of the drilling and production system; and
    sampling the same drilling fluid after the drilling fluid exits a borehole of the drilling and production system.

19. The method of claim 14, further comprising producing a downhole spectrogram from the downhole chromophoric signal and an uphole spectrogram from the uphole chromophoric signal.

20. The method of claim 14, further comprising contacting the uphole and downhole Friedel-Crafts reaction products with an electromagnetic signal from an integrating sphere.

* * * * *